United States Patent [19]
Rabenecker et al.

[11] 3,933,029
[45] Jan. 20, 1976

[54] GAS DETECTOR WITH AUTOMATICALLY OPERABLE FAN SWITCH

[75] Inventors: Horst Rabenecker, Bad Schwartau; Horst Spahrbier, Lübeck, both of Germany

[73] Assignee: Drägerwerk Aktiengesellschaft, Germany

[22] Filed: Jan. 18, 1974

[21] Appl. No.: 434,411

[30] Foreign Application Priority Data
Jan. 26, 1973 Germany............................ 2303710

[52] U.S. Cl................................ 73/23; 73/421.5 R
[51] Int. Cl.²........................................... G01N 1/22
[58] Field of Search........................... 73/23, 421.5 R

[56] References Cited
UNITED STATES PATENTS 3,266,293  8/1966  Hubner.................................. 73/23
3,343,402  9/1967  Hubner.................................. 73/23
3,391,570  7/1968  Becker et al.......................... 73/23
3,427,862  2/1969  Hubner.................................. 73/23

FOREIGN PATENTS OR APPLICATIONS
1,188,607  4/1970  United Kingdom............ 73/421.5 R Primary Examiner—Charles A. Ruehl
Attorney, Agent, or Firm—McGlew and Tuttle

[57] ABSTRACT

A gas detector, comprises a housing having an interior cavity with a wall having a testing tube receiver with an opening therethrough into the cavity. Spaced above the wall and in alignment therewith, is a test tube receiving tube and, when a test tube is placed in the receiving tube, it actuates a switch to actuate a fan to draw a gas sample through the testing tube for testing purposes.

5 Claims, 3 Drawing Figures

GAS DETECTOR WITH AUTOMATICALLY OPERABLE FAN SWITCH

BACKGROUND OF THE INVENTION

FIELD OF THE INVENTION

This invention relates in general to the construction of gas detecting devices and, in particular, to a new and useful device for detecting gases of predetermined types which includes means for mounting a testing tube on a housing over a receiver having an opening therethrough and with a sleeve mounted above the opening in a position so that when a testing tube is positioned in the sleeve, a switch is actuated to operate a fan to draw air through the tube.

REFERENCE TO PRIOR APPLICATION

This invention is an improvement over the invention described and claimed in application Ser. No. 376,291, filed on July 5, 1973 by inventors Kurt Leichnitz, Bernd Mussmann and Horst Rabenecker, now abandoned.

DESCRIPTION OF THE PRIOR ART

Gas detectors are known, and the present invention is an improvement over U.S. application Ser. No. 376,291 which comprises a gas detector having an electrically driven air propelling device or fan and a connection for an indicator tube which tube is positioned over a cavity in a housing containing the fan and which is effective to draw air in through the tube when testing is to take place. The aforementioned patent application also describes a portable type gas detector which includes a housing adapted to be carried on the body of the user and a battery operated small size fan, as well as a connection for the insertion of an indicator tube in position over a cavity in the housing. The patent application is directed to a lightweight gas detector which is simple in construction and which may be carried along, for example, by a working team for example, in a mine, and gives an instant indication of noxious substances contained in the air of the entered space.

SUMMARY OF THE INVENTION

The present invention is an improvement over the previous application inasmuch as it provides a means for centering a testing tube over a cavity of the housing and which includes means associated with the centering means for turning on a fan for circulating the testing air through the testing tube. The construction is such that when the tube is inserted in a sleeve, a switching circuit is closed to actuate the fan. The invention has the advantage of further simplifying the construction of the known detector, and it assures that when the tube is in place, the air propelling device is switched on, and while the testing tube is removed, the air propelling device will be switched off. In a particularly simple embodiment of the invention, the switching element is arranged so that when the tube is connected to the housing containing the fan, the switching circuit is closed.

In accordance with a feature of the invention, the housing includes a back wall which closes a compartment containing a battery or dry cell for operating the fan and which continues behind an exposed corner of the housing behind a support wall for supporting a testing tube which is held in an upright position by a holding tube or sleeve supported on a bracket affixed to the back wall. The back wall also forms a shield between the testing tube and the user's body or garment.

Still another construction is useful in which the guideway shields the opened top of the testing tube so that any damage which might be caused by this open top glass end is avoided.

In order to facilitate carrying of the device by the user, the back wall is provided with a holding clip.

Accordingly, it is an object of the invention to provide a gas detector which comprises a housing having a battery operated fan with a receiver opening communicating to the interior of the housing and with means at the receiver opening for receiving a testing tube having switching means for actuating the fan whenever the testing tube is in position.

A further object of the invention is to provide a device for testing a surrounding gas such as the surrounding air of the atmosphere which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there is illustrated a preferred embodiment of the invention.

GENERAL DESCRIPTION OF A PREFERRED EMBODIMENT

Figure 1:
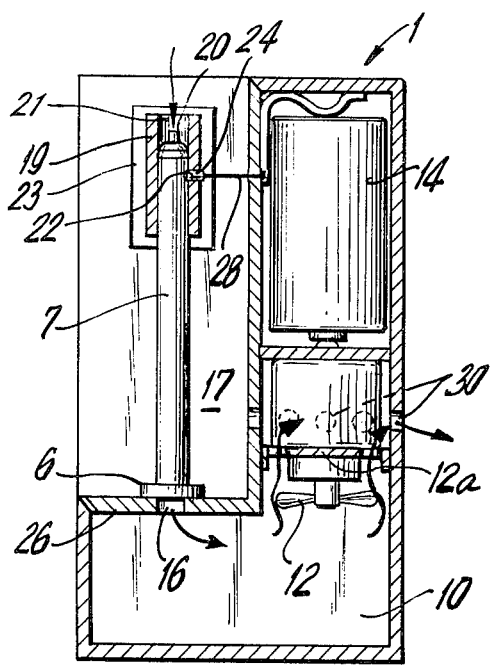
FIG. 1 is a transverse section of a gas detector constructed in accordance with the invention.
Figure 2:
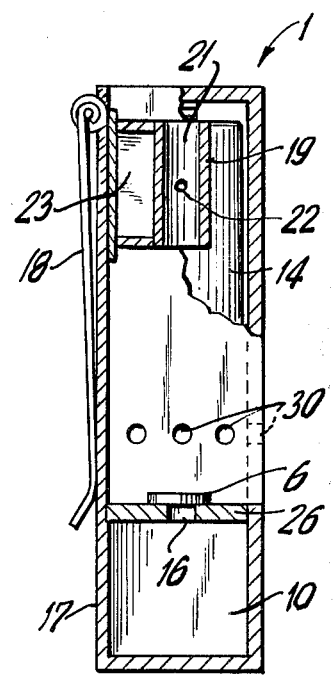
FIG. 2 is a section taken along the line 2—2 of FIG. 3 with the testing tube removed.
Figure 3:
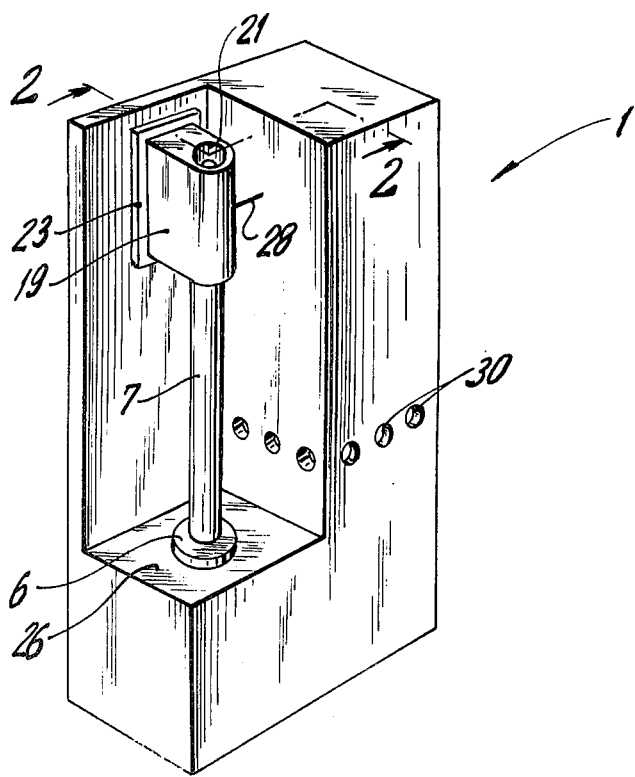
FIG. 3 is a front end perspective view of the device shown in FIGS. 1 and 2.

Referring to the drawings in particular, the invention embodied therein, comprises a housing, generally designated 1, which includes a cavity 10 containing a small size fan 12, arranged at a spaced location from a power cell or battery 14. The battery 14 is connected to operate fan 12 to cause it to draw air in through a receiver opening 16 having a receiver fitting 6 for receiving testing tube 7. Testing tube 7 is of a known indicator type which has a material, which for example gives a visual change when it is exposed to gases of certain types. The top of testing tube 7 is open to permit the inflow of a gas sample when fan 12 is operated.

In accordance with the invention, a holding tube or sleeve 19 includes switch means 24 associated therewith, which is connected to battery 14 in order to connect the battery to fan 12 to operate it. In the embodiment illustrated, housing 1 includes a back wall or shield 17 which provides a protection between testing tube 7 and the user of the device, and the wall is provided with a clip 18 in order to permit the device to be secured, for example, to a user's clothing. Directly ahead of back wall 17 is a support wall 26 having the receiver 6 thereon.

In accordance with a feature of the invention the switch means 24 is located in an opening 22 which extends into the bore or passage 21 of the holding tube or sleeve 19 so that its actuator extends outwardly into the passage 21 of the holding tube in a position to be contacted by the testing tube 7 which is positioned so that its upper portion extends therethrough. Holding tube 19 is mounted on a bracket 23 arranged above and in alignment with the support wall 26. Testing tube receiver means includes the holding tube 19 which receives the upper end of the testingg tube 7 and the receiver fitting 6 having an opening therethrough which is aligned with the receiver opening 16 in the support wall 26 and supports the bottom of the testing tube 7. The space above the support wall 26 is opened frontally, to one side and upwardly so as to permit insertion and removal of the testing tube on the receiver fitting 6 and through the holding tube 19. The switch member 24 is connected by a cable 28 to the battery 14. When a testing tube 7 is placed in a position to extend within the bore 21 of the holding tube 19 with its base supported on the receiver fitting 6, it actuates switch member 24 to actuate fan 12 and causes air to be circulated downwardly through opening 20 of the tube 7 and through the opening 16 of the support wall 26 into the interior cavity 10 of the housing. The air which is drawn into the cavity 10 is moved over the fan 12 and a support bracket or spider 12a and is charged out of the cavity 10 through a series of openings 30 located between the battery 14 and the fan 12.

Holding tube or sleeve 19 is sized and spaced from receiver fitting 6 so that it covers the opened end 20 of the testing tube and thus, this opened or broken end is protected.

Switch 24 is actuated when a testing tube 7 is positioned in holding tube 19 to start fan 12 and it is deactuated when the testing tube is removed from holding tube 19 to cause fan 12 to stop.

While a specific embodiment of the invention has been shown and described in detail to illustrate the application of the principles of the invention, it will be understood that the invention may be embodied otherwise without departing from such principles.

What is claimed is:

1. A gas detector for use with a gas testing tube into which the gas is delivered and which indicates the presence of preselected gases, comprising a housing having an interior cavity and a support wall having a testing tube receiver fitting with an opening therethrough into the cavity, means for holding the testing tube over the receiver fitting, a fan in said housing for drawing a gas sample through the testing tube and receiver fitting and into said cavity, a power cell in said housing, and switch means associated with said testing tube holding means and responsive to insertion of the testing tube therein to connect said power cell to said fan to operate said fan, said testing tube holding means comprising a sleeve carried on said housing and located in alignment with and spaced above said receiver fitting.

2. A gas detector, according to claim 1, wherein said switch means is located within said sleeve.

3. A gas detector, according to claim 1, wherein said power cell comprises a flash light battery located in said cavity in spaced relationship to said fan, at least one opening in said housing between said fan and said battery for the discharge of air.

4. A gas detector for use with a gas testing tube into which the gas is delivered and which indicates the presence of preselected gases and adapted to be worn by a user of the detector, comprising a housing having an interior cavity and a support wall having a testing tube receiver fitting with an opening therethrough into the cavity, means connected to a back wall of said housing for holding the testing tube over the receiver fitting, a fan in said housing for drawing a gas sample through the testing tube and receiver fitting and into said cavity, a power cell in said housing, and switch means associated with said testing tube holding means and responsive to insertion of the testing tube therein to connect said power cell to said fan to operate said fan, means on said back wall for clipping said housing to the user of the gas detector, said back wall providing a personal shield between said testing tube and the user.

5. A gas detector for use with a gas testing tube into which the gas is delivered and which indicates the presence of preselected gases and adapted to be worn by a user of the detector, comprising a housing having an interior cavity and a support wall having a testing tube receiver fitting with an opening therethrough into the cavity, means for holding the testing tube over the receiver fitting, a fan in said housing for drawing a gas sample through the testing tube and receiver fitting and into said cavity, a power cell in said housing, and switch means associated with said testing tube holding means and responsive to insertion of the testing tube therein to connect said power cell to said fan to operate said fan, said testing tube holder means comprising a sleeve carried on said housing spaced from said receiver fitting and in alignment therewith and being at a height above the fitting such that it covers the top of the testing tube held thereby.

* * * * *